United States Patent
Fleischer et al.

[11] Patent Number: 5,767,388
[45] Date of Patent: *Jun. 16, 1998

[54] METHANE SENSOR AND METHOD FOR OPERATING A SENSOR

[75] Inventors: Maximilian Fleischer, Höhenkirchen; Hans Meixner, Haar, both of Germany

[73] Assignee: Siemens Aktiengesellschaft, Munich, Germany

[*] Notice: The term of this patent shall not extend beyond the expiration date of Pat. No. 5,635,628.

[21] Appl. No.: 734,131

[22] Filed: Oct. 21, 1996

Related U.S. Application Data

[63] Continuation of Ser. No. 429,035, Apr. 26, 1995, abandoned which is a continuation of PCT/DE94/00360, Mar. 30, 1994.

[51] Int. Cl.$^6$ .................................................. G01N 27/12
[52] U.S. Cl. ........................ 73/31.06; 73/23.31; 73/338; 73/34
[58] Field of Search .................... 73/23.31, 31.05, 73/31.06; 338/34; 422/88, 95, 94; 436/141

[56] References Cited

U.S. PATENT DOCUMENTS

| | | | |
|---|---|---|---|
| 4,535,315 | 8/1985 | Sakai | 73/31.06 X |
| 4,535,316 | 8/1985 | Wertheimer et al. | 73/31.05 X |
| 4,732,738 | 3/1988 | Nakatani et al. | 73/31.05 X |
| 5,635,628 | 6/1997 | Fleischer et al. | 73/31.06 |

FOREIGN PATENT DOCUMENTS

| | | |
|---|---|---|
| 0464243 | 1/1992 | European Pat. Off. |
| 0464244 | 1/1992 | European Pat. Off. |
| 0488352 | 6/1992 | European Pat. Off. |
| 0527258 | 2/1993 | European Pat. Off. |
| 7601120 | 1/1976 | France |
| 1280809 | 7/1972 | United Kingdom |
| 2112525 | 6/1981 | United Kingdom |

OTHER PUBLICATIONS

"Solid State Gas Sensors", Moseley et al., The Adam Hilger Series on Sensors, 1987, pp. 17–31.

*Primary Examiner*—Michael Brock
*Attorney, Agent, or Firm*—Herbert L. Lerner; Laurence A. Greenberg

[57] ABSTRACT

A sensor has a temperature in a range from 700° to 850° C. for detecting methane, and an oxygen-sensitive semiconducting metal oxide. A method for operating a gas sensor having two electrodes, an oxygen-sensitive semiconducting metal oxide conductively connecting the electrodes to one another, and a heating element, includes heating the metal oxide to a constant temperature in a range from 700° to 850° C., and measuring the resistance, conductivity or relative permeability of the metal oxide.

7 Claims, 3 Drawing Sheets

METHANE SENSOR AND METHOD FOR OPERATING A SENSOR

This application is a continuation of application Ser. No. 08/429,035, filed on Apr. 26, 1995, now abandoned.

CROSS-REFERENCE TO RELATED APPLICATION

This application is a Continuation of International Application Ser. No. PCT/DE94/00360, filed Mar. 30, 1994.

BACKGROUND OF THE INVENTION

Filed of the Invention

The invention relates to a a methane sensor and a method for operating a gas sensor having two electrodes being conductively connected to one another by an oxygen-sensitive semiconducting metal oxide, and a heating element.

In order to continuously monitor the methane concentration in air, gas sensors based on semiconducting metal oxides (see, for example, U.K. Patent Specification 1 280 809) and reaction heat or heat-color sensors (see "Solid-State Gas Sensors", edited by P. T. Moseley and B. C. Tofield, from the Adam Hilger Series on Sensors, edited by E. Jones, IOP Publishing Ltd., 1987, pp. 17–31) are predominantly used.

Semiconductor gas sensors typically have a ceramic base body with a surface on which two electrodes and the metal oxide that conductively connects the electrodes are disposed. A resistor element present on the back side of the base body enables heating of the sensor to a temperature in the range from approximately 100° to 500° C. If a certain gas flows across the thermally activated sensor material, then its resistance or conductance changes as a result of complicated adsorption processes at the surface. The concentration of the particular gas can therefore be determined easily be measuring the resistance or conductance.

The most frequently used metal oxide is tin oxide, which is semiconducting beyond a temperature of approximately 350° C. It can be sensitized for various gases by means of suitable doping. In order to detect methane, platinum is, for instance, used as the dopant and the greatest sensitivity occurs at a sensor temperature of 500° C.

Pellistors used to detect methane and other hydrocarbons typically use a platinum wire embedded in a ceramic composition as the measuring element and use means for heating the sensor to an operating temperature in the range from approximately 300° to 500° C. The surface of the ceramic is coated with a catalyst. If the ambient air contains an oxidizable gas, the gas burns catalytically at the sensor surface. As a consequence of the heat of combustion which is liberated, the sensor temperature and therefore the resistance of the platinum wire as well rise in accordance with the concentration of the oxidizable gas in the ambient air.

The effect of the catalyst on the sensor surface can decrease over time. That situation substantially limits the surface life of pellistors to an average of 1 to 2 years. Their functional capability is also impaired by the presence of catalyst poisons in the ambient air. Moreover, evaluating the output signal of a pellistor presents considerable difficulties. For instance, the sensor signal initially rises with the methane concentration, but beyond a certain limit value becomes smaller despite a higher gas concentration. Additional evaluation electronics are therefore needed in order to assure unequivocal interpretation of the measurement signal over the entire range of concentration from 0 to 100 volume percent. Since the metal oxide films used in semiconductor gas sensors are also subject to chemical changes, both types of detector must be re-procured repeatedly.

European Patent Application 0 464 243 A1 describes an oxygen detector with a catalytically inactive sensor film of gallium oxide. The operating temperature of that detector is preferably in a range from 850° to 1000° C., where the oxygen in the crystal lattice of the metal oxide is in thermodynamic equilibrium with the oxygen in the ambient atmosphere. Since the number of oxygen voids in the crystal lattice, and therefore also the number of freely movable electrons, depends on the particular oxygen partial pressure, any change in oxygen concentration causes a corresponding change in the conductivity of the gallium oxide. At lower temperatures ($T \leq 700°$ C.), the oxygen void equilibrium is frozen, and therefore the detector no longer responds to changes in the oxygen partial pressure.

Hydrogen and other reducing gases adsorb on the surface of the gallium oxide. If the adsorption takes place by way of a chemical bond to the gallium oxide surface (chemisorption), then the adsorbate molecules give up electrons to the semiconducting metal oxide, and as a result its conductivity rises. The function of the gallium oxide sensor for reducing gases known from European Patent Application 0 464 244 A1 is based on that mechanism. In the temperature range from approximately 400° to 650° C., the sensor responds to both hydrogen and carbon monoxide. Moreover, a strong cross-sensitivity to water vapor is observed, since water molecules can also be adsorbed in laden fashion.

SUMMARY OF THE INVENTION

It is accordingly an object of the invention to provide a methane sensor and a method for operating a sensor, which overcome the hereinafore-mentioned disadvantages of the heretofore-known devices and methods of this general type and which expand the possible uses of gas sensors that contain an oxygen-sensitive semiconducting metal oxide as their sensitive material.

With the foregoing and other objects in view there is provided, in accordance with the invention, a sensor having a temperature in a range from 700° to 850° C. for detecting methane, comprising an oxygen-sensitive semiconducting metal oxide.

With the objects of the invention in view, there is also provided a method for operating a gas sensor having two electrodes, an oxygen-sensitive semiconducting metal oxide conductively connecting the electrodes to one another, and a heating element, the improvement which comprises heating the metal oxide to a constant temperature in a range from 700° to 850° C., and measuring a parameter of the metal oxide selected from the group consisting of resistance, conductivity and relative permeability.

In accordance with a concomitant mode of the invention, there is provided a method which comprises heating the metal oxide to a temperature of 775° C.

If the sensor is operated at a temperature in the range from 700° to 850° C., in particular 775° C., the semiconducting metal oxide then reacts extremely sensitively to methane and has no substantial cross-sensitivity to other reducing gases and water vapor. Therefore, the sensor can advantageously be used for continuous methane concentration monitoring in the home (for finding leaks in a natural gas line or a defect in a gas stove), or in mines to warn of firedamp if mine gas is produced.

Other features which are considered as characteristic for the invention are set forth in the appended claims.

Although the invention is illustrated and described herein as embodied in a methane sensor and a method for operating a sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1A:
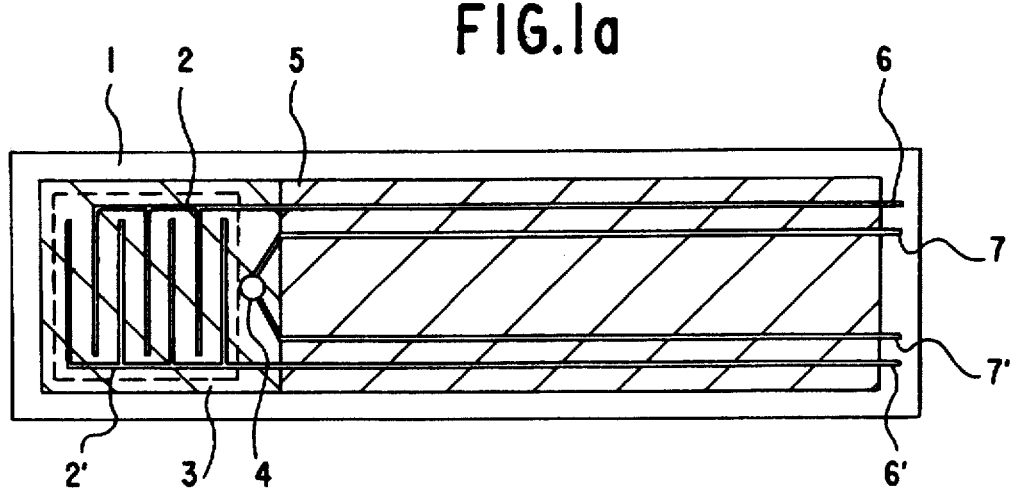
FIGS. 1a, 1b and 1c are diagrammatic, sectional views of a known gallium oxide gas sensor.
Figure 1B:
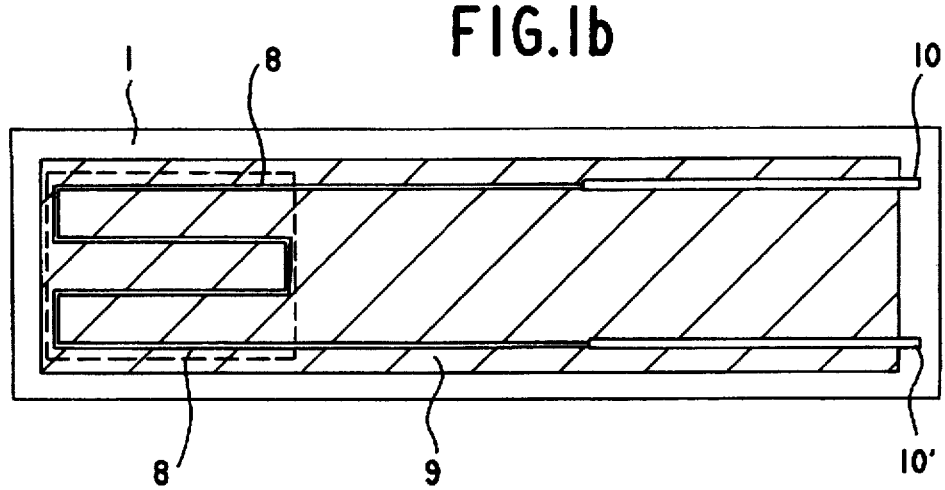
Figure 1C:
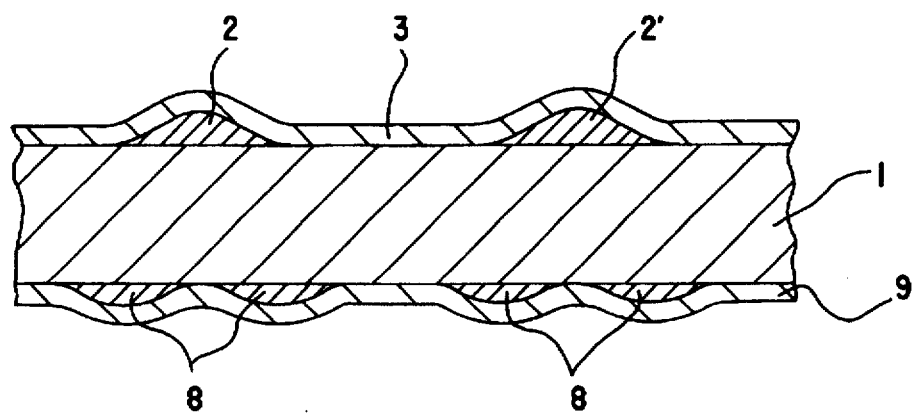

Referring now to the figures of the drawing in detail and first, particularly, to FIG. 1 thereof, there is seen a gas sensor which is known from European Patent Applications 0 464 243 A1 and 0 464 244 A1 and has a substrate plate 1 of beryllium oxide, aluminum oxide or magnesium oxide. Disposed on the surface of the substrate plate 1 are two platinum electrodes 2, 2' forming an interdigital structure, one gallium oxide layer 3 that covers those electrodes and is approximately 1 to 2 μm thick, and one thermocouple 4 (see also FIG. 1c, which shows the detector in section). A passivation layer of glass, metal oxide or silicon oxide, which is indicated by reference numeral 5, shields platinum lead lines 6, 6' and 7, 7' which are respectively associated with the electrodes 2, 2' and the thermocouple 4, from the oxygen in the ambient atmosphere. A resistance loop 8 which is disposed on the back side of the substrate plate 1, as is seen in FIG. 1b, is used as a heating element. The resistance loop has a spiral or meander-shaped structure and is likewise provided with a passivation layer 9. Connection to the external heating current supply is made through low-resistance conductor tracks 10, 10'.

In the illustrated exemplary embodiment, the platinum electrodes 2, 2' are disposed directly on the surface of the substrate plate 1. Naturally, it is also possible to provide an additional insulating layer of silicon oxide between the substrate plate 1 and the electrodes 2, 2', or to embed the electrodes 2, 2' completely within the gallium oxide layer 3.

Figure 2:
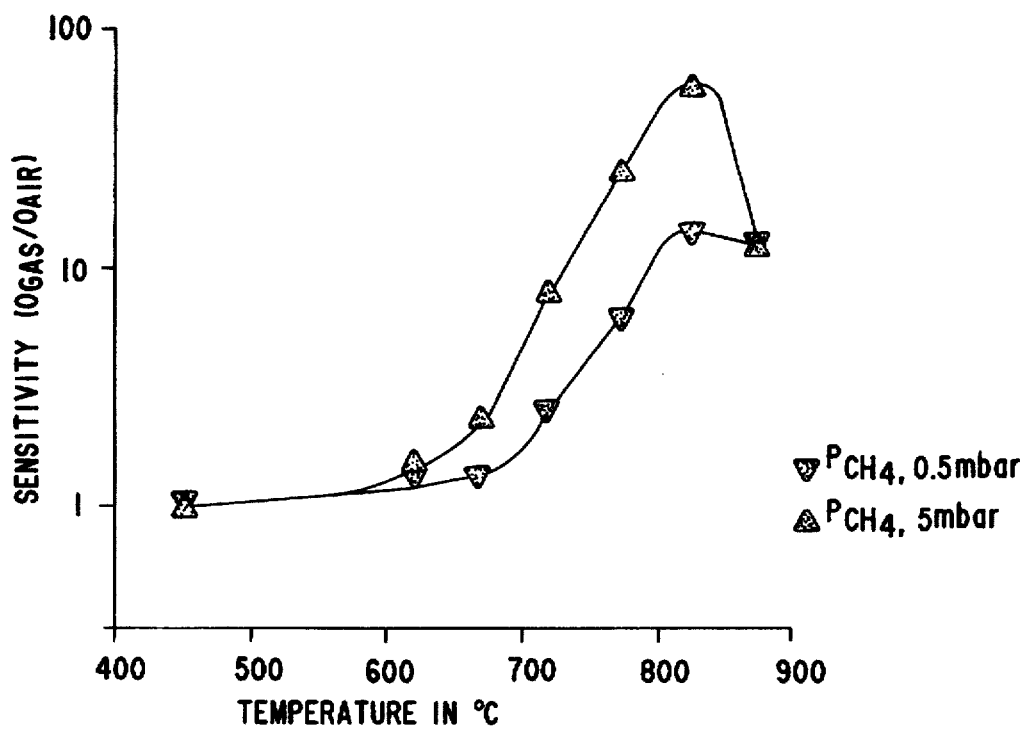
FIG. 2 is a graph showing the temperature dependency of the sensitivity of the gallium oxide sensor to methane in air.

The known sensor has high sensitivity to methane, if the gallium oxide is heated with the aid of the resistance loop 8 to a temperature in the range between 700° and 850° C. FIG. 2 shows the measured temperature dependency of the sensitivity for various concentrations of methane in moist air. The sensitivity is defined by the following quotient:

$$\sigma_{gas}/\sigma_{air}$$

wherein:

$\sigma_{gas}$=sensor conductivity in the gas being measured; and $\sigma_{air}$=sensor conductivity in air. The maximum sensitivity is at approximately 800° C.

Figure 3:
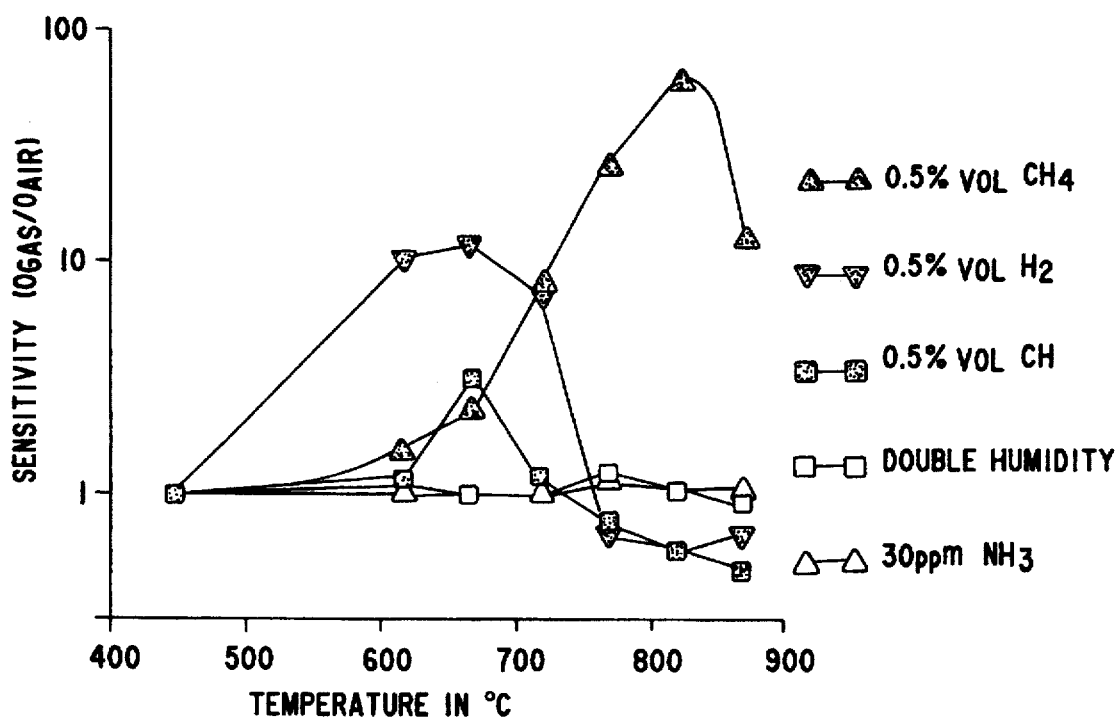
FIG. 3 is a graph showing the temperature dependency of the sensitivity of the gallium oxide sensor to reducing gases.

As FIG. 3 indicates, at temperatures above approximately 750° C., the sensor exhibits no cross-sensitivity with respect to the reducing gases being formed of hydrogen, carbon monoxide and ammonia. That is because, among other reasons, the number of the chemisorbed molecules decreases as the temperature increases, for energy reasons. At temperatures above 750° C., the chemisorption on $Ga_2O_3$ evidently comes to a stop, which prevents a change in the conductance based on that process. Unlike hydrogen, carbon monoxide or ammonia, methane, with its stable tetrahedron configuration, cannot be chemisorbed on the surface of the semiconducting metal oxide. However, at sufficiently high temperatures it does react with the oxygen of the metal oxide (oxidation of the methane), so that oxygen voids are created on the surface. Those voids give up freely movable electrons to the crystal lattice, and as a result the conductivity of the metal oxide rises.

In the temperature range from 750° to 800° C., the gallium oxide detector has a cross-sensitivity to the oxygen in the ambient atmosphere. However, that is no detriment for detecting methane in air, since the oxygen partial pressure is constant, at 0.2 bar. However, even if the oxygen partial pressure should vary to a slight extent, the resultant sensor reaction is very small in comparison to its reaction to methane. For instance, a 10% change in the oxygen partial pressure causes a conductance change by the factor 1.8. Conversely, a change in the methane concentration by 0.5%, causes a conductance change by a factor of nearly 50.

Figure 4:
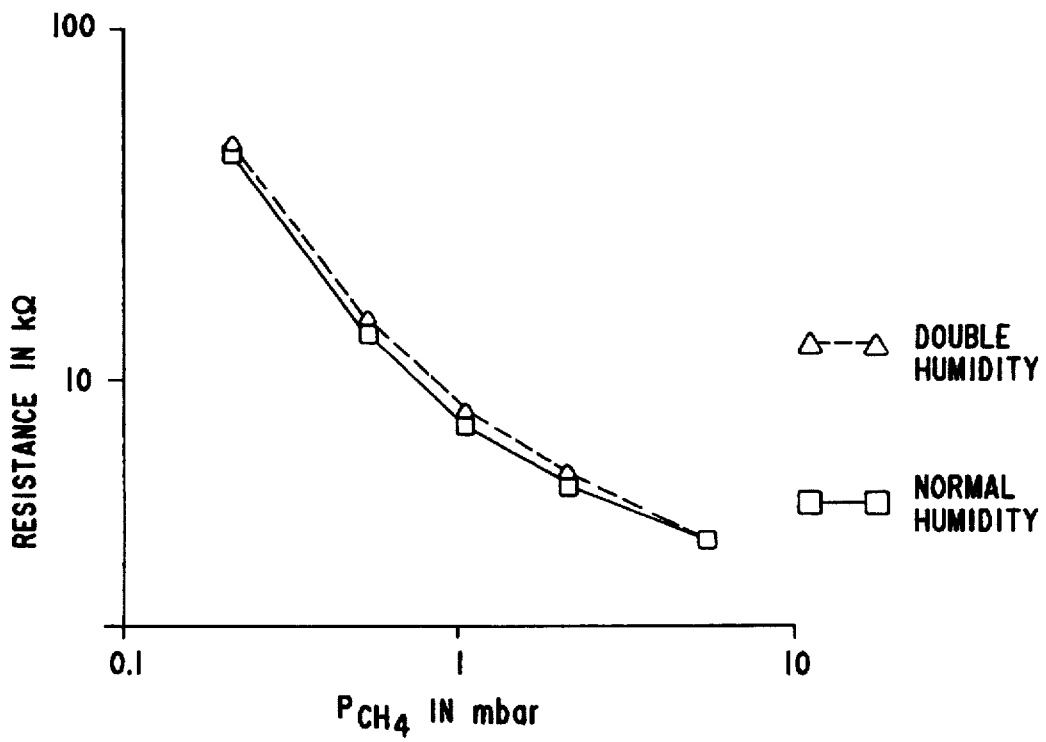
FIG. 4 is a graph showing the characteristic curve of the gallium oxide sensor as a function of moisture in air.

FIG. 4 shows the influence of the moisture in the air on the characteristic curve of the sensor. The resistance of the sensor is plotted as a function of the partial pressure of the methane at a temperature of T=800° C. It is clear from that diagram that the characteristic curve of the methane detector hardly changes (see also the measurement values indicated by squares in FIG. 3) if the water proportion is doubled from a partial pressure of 7.85 mbar (normal humidity) to 15.7 mbar partial pressure (twice the humidity).

Figure 5:
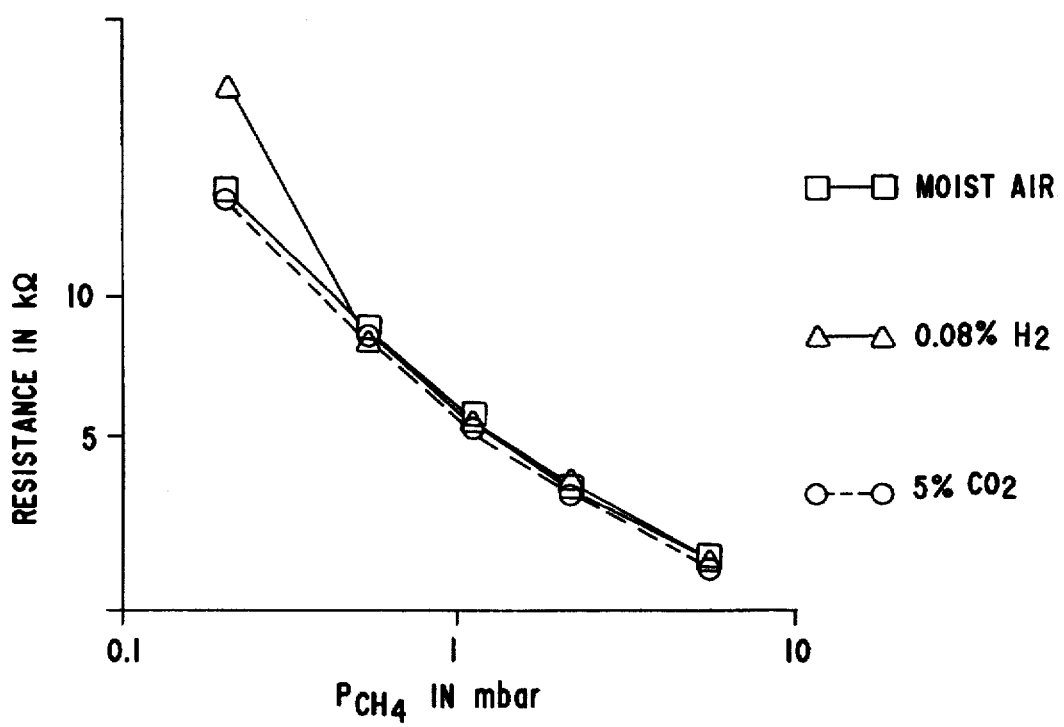
FIG. 5 is a graph showing the influence of interfering gases on the characteristic curve of the sensor.

Carbon dioxide, which can certainly occur in higher concentrations in the atmosphere, also has no effect on the characteristic curve of the methane sensor (see FIG. 5). It is only at very slight methane concentrations that a cross-sensitivity to hydrogen is observed.

The methane sensor described above meets the stringent demands for an unequivocal measurement signal even at higher measurement concentrations. Moreover, it does not react to other reducing gases or to the moisture in air. The detector is therefore particularly usable in the home and in mining for continuous monitoring of the methane concentration in air. A single sensor element suffices, and it is unnecessary to employ a plurality of different measurement methods. Since the method of thin-film technology may be employed in manufacturing the sensor, the sensor can be made economically and with good replicability in large mass-produced quantities.

The invention is naturally not limited to the exemplary embodiment described herein. For instance, it is also readily possible to heat the gas sensor known from U.K. Patent Specification 1 529 461, corresponding to U.S. Pat. No. 4,057,996, to the indicated operating temperature and to use it as a methane detector.

In the temperature range from 700° to 850° C., sensors of the kind that employ $TiO_2$, $Fe_2O_3$, $CeO_3$, $SrTiO_3$, $Nb_2O_3$ or $HfO_2$, instead of $Ga_2O_3$, for instance, can in particular also be used as methane detectors. Those materials are each oxygen-sensitive semiconducting metal oxides that are thermally stable in the temperature range given.

We claim:

1. A method for detecting methane in a gas mixture, which comprises:

providing a gas sensor having two electrodes, an oxygen-sensitive semiconducting metal oxide conductively connecting the electrodes to one another, and a heating element, adjusting an operating temperature of the gas sensor to between 750° and 850° C., and exposing the gas sensor to the gas mixture;

heating the metal oxide to a constant temperature in a range from 750° to 850° C., reacting methane in the gas mixture with oxygen of the metal oxide, and measuring a parameter of the metal oxide dependent on a methane concentration in the gas mixture, the parameter being selected from the group consisting of resistance, conductivity and relative permeability.

2. The method according to claim 1, which comprises heating the metal oxide to a temperature of 775° C.

3. The method according to claim 1, which comprises: selecting the semiconductor metal oxide from the group consisting of $Fe_2O_3$, $CeO_3$, $SrTio_3$, $Nb_2O_3$, $Ga_2O_3$, and $HfO_2$.

4. The method according to claim 1, which comprises: providing $TiO_2$ as the semiconductor metal oxide.

5. A methane sensor, comprising:

means for detecting methane in a gas mixture, said means being an oxygen-sensitive semiconducting metal oxide; and a heater connected to said oxygen-sensitive semiconducting metal oxide for heating said oxygen-sensitive semiconducting metal oxide to a temperature in a range from 750° to 850° C., and means for measuring a parameter of the metal oxide dependent on a methane concentration in the gas mixture, the parameter being selected from the group consisting of resistance, conductivity and relative permeability, wherein a change in the parameter is caused by a reaction of the methane with oxygen of said semiconducting metal oxide.

6. The sensor according to claim 5, wherein said oxygen-sensitive semiconducting metal oxide is a oxygen-sensitive semiconducting metal oxide selected from the group consisting of $Fe_2O_3$, $CeO_3$, $SrTio_3$, $Nb_2O_3$, $Ga_2O_3$, and $HfO_2$.

7. The sensor according to claim 5, wherein said oxygen-sensitive semiconducting metal oxide is $TiO_2$.

* * * * *

UNITED STATES PATENT AND TRADEMARK OFFICE
CERTIFICATE OF CORRECTION

PATENT NO.    : 5,767,388
DATED         : June 16, 1998
INVENTOR(S)   : Maximilian Fleischer et al.

It is certified that error appears in the above-identified patent and that said Letters Patent is hereby corrected as shown below:

Title page,
Item [30] should be inserted as follows:

-- Apr. 2, 1993  [DE]   Germany .....   P43 10 914.4 --

Signed and Sealed this

Twenty-first Day of May, 2002

Attest:

Attesting Officer

JAMES E. ROGAN
Director of the United States Patent and Trademark Office